United States Patent [19]

Hocherl et al.

[11] Patent Number: 5,556,424
[45] Date of Patent: Sep. 17, 1996

[54] LEAD EXTRACTOR WITH BEVELLED CLAMP

[75] Inventors: Manfred Hocherl, Efringen-Kirchen; Jorg Reinhardt, Grenzach-Whylen, both of Germany

[73] Assignee: VascoMed Institut fur Kathetertechnologie GmbH, D-79576 Weil am Rhein, Germany

[21] Appl. No.: 344,136

[22] Filed: Nov. 23, 1994

[30] Foreign Application Priority Data

Nov. 25, 1993 [DE] Germany .......................... 43 40 151.1

[51] Int. Cl.⁶ ............................. A61N 1/04; A61N 1/02; A61N 1/372
[52] U.S. Cl. ........................... 607/116; 607/119; 128/897
[58] Field of Search ........................... 128/899, 897, 128/757; 607/116, 119, 126; 606/159

[56] References Cited

U.S. PATENT DOCUMENTS

| | | | |
|---|---|---|---|
| 4,765,332 | 8/1988 | Fischell et al. | 606/159 |
| 4,874,375 | 10/1989 | Ellison | 604/164 |
| 5,013,310 | 5/1991 | Goode et al. | 607/119 |
| 5,344,439 | 9/1994 | Otten | 607/126 |
| 5,360,441 | 11/1994 | Otten | 607/116 |
| 5,370,650 | 12/1994 | Tovey et al. | 128/899 |

FOREIGN PATENT DOCUMENTS

| | | | |
|---|---|---|---|
| 0368568 | 2/1989 | European Pat. Off. | A61N 1/05 |
| 269199A | 10/1993 | Japan | 606/159 |

OTHER PUBLICATIONS

"Pacemaker Electrode Explanation Set", Various Cardiology Procedures, William Cook Europe A/S.

*Primary Examiner*—William E. Kamm
*Assistant Examiner*—Carl H. Layno
*Attorney, Agent, or Firm*—Baker & Daniels

[57] ABSTRACT

An extractor consisting essentially of a guide barrel, a clamping element and a pull wire. The bordering end faces of the guide barrel and clamping element feature each a bevel which is complementary in design to the other. The pull wire is joined to the clamping element. The clamping element is moved on the bevel in the direction of the proximal end of the extractor by application of traction force on the pull wire, thereby enlarging the greatest outside diameter of the guide barrel in the area of the bevel. The relatively long design of the bevels assures with low traction forces an anchoring of the extractor in an electrode spiral by frictional engagement.

10 Claims, 5 Drawing Sheets

LEAD EXTRACTOR WITH BEVELLED CLAMP

BACKGROUND OF THE INVENTION

1. Field of the Invention

The invention concerns an extractor, and, more particularly, an extractor for extraction of cardiac pacemaker electrodes of spiral structure that have been implanted in tissue. Such extractors are generally configured with a flexible guide barrel which on its proximal end is joined to a handle element and whose distal front face is angled so as to form a bevel in relation to the longitudinal axis of the guide barrel, and with a pull wire running in the guide barrel and having a clamping element arranged on its distal end, the front face of said clamping element facing the guide barrel having a design which is essentially complementary to the distal front face of the guide barrel.

2. Description of the Prior Art

An extractor of the above described type is being marketed by the firm William Cook Europe A/S, Bjaeverskov, Denmark, designated as "Extension Hook" (order No. EXH-0.5-70). Relevant flyers were distributed on Jun. 27, 1992, at the convention "Cardiac Pacemaker Infections—Prevention, Diagnostic and Therapy" sponsored by the Clinic III for Internal Medicine at the University of Cologne. The pull wire is on its distal end joined firmly to the clamping element. The outside diameter of the clamping element essentially matches the outside diameter of the guide barrel.

The proximal end of the pull wire is in mesh with a puller so that, as a pulling force is applied on the pull wire, the clamping element can be moved from its initially coaxial arrangement in relation to the guide barrel to a position which is laterally offset relative to the longitudinal axis of the guide barrel. Designed in essentially complementary fashion in respect to their bevels, the bordering end faces of the guide barrel and clamping element serve as an area of movement. The outside diameter of the guide barrel is in the area of its distal bevel enlarged in one direction by offset of the clamping element in its arrangement relative to the guide barrel, making the distal area of the guide barrel introduced in an electrode spiral clampable within said electrode. The cardiac pacemaker electrode spiral is then extractable.

To enable an easy insertion of the guide barrel with the clamping element in the electrode spiral, the clamping element requires a coaxial arrangement relative to the guide barrel. The pull wire running in the guide barrel, therefore, is appropriately rigid under thrust. Owing to the very small outside diameter of the guide barrel—about 0.4 mm—, the pull wire diameter, therefore, can be only slightly smaller than the inside diameter of the guide barrel, so as to assure sufficient flexural strength. The available offset of the clamping element relative to the guide barrel, on the prior extractor, leads to a diameter enhancement in one direction by about 20%. Therefore, the extractor is suited to pull electrode spirals whose inside diameter is smaller than the 20%-enlarged diameter of the guide barrel in the area of the bevel. To achieve greater offsets, which notably with flexible electrode spirals is absolutely necessary for sufficient anchoring, thinner pull wires could be used, but these would then no longer possess the necessary flexural strength.

What is needed is an extractor that is capable of providing easy insertion in an electrode spiral, and that not only possesses sufficient flexural strength, but which extractor enables even in flexible electrode spirals a frictional-engagement anchoring of their distal areas.

SUMMARY OF THE INVENTION

This problem is inventionally solved in that, basing on the bevel area pointing to the handle element, a recess is provided which follows the axial extension of the guide barrel, and in that the axial extension of the distal bevel of the guide barrel corresponds to a multiple of the outside diameter of the guide barrel.

Since the guide barrel, basing on the bevel area facing toward the handle element, features a recess that follows its longitudinal extension, the movability of the clamping element by the pull wire is not limited to a partial section contained on the bevel, but it is now also possible to place the clamping element sideways beside the guide barrel. With the clamping element having essentially the same outside diameter as the guide barrel, the diameter of the guide barrel in its bevel area can nearly be doubled and, thus, the clamping element be used also in very flexible electrode spirals.

Moreover, since the bevel of the distal end face of the guide barrel forms with its longitudinal axis a shallow angle, a relatively large contact surface is assured, by way of which a frictional engagement between the clamping element, or guide barrel, and the inside of the electrode spiral can be established. An effective anchoring of the guide barrel is thus possible also in stiff electrode spirals.

In a preferred embodiment, the width of the recess matches essentially the diameter of the pull wire. The longitudinal extension of the recess is chosen sufficiently long, allowing the clamping element to be placed sideways beside the guide barrel, depending on the flexural strength of the pull wire. The bevel of the guide barrel inscribes with its longitudinal axis an angle between 3° and 30° with angles between 5° and 10° being preferred.

In another embodiment, the clamping element is a section of the guide barrel. Basing on the bevel area away from the guide barrel, the clamping element also features a recess that follows its axial extension.

An advantage of the present invention is that it provides an extractor whose pull wire, in order to guarantee easy insertion in an electrode spiral, not only possesses sufficient flexural strength, but which extractor enables even in flexible electrode spirals a frictional-engagement anchoring of their distal areas.

In a further embodiment of the extractor, a tubular intermediate segment is provided between the clamping element and the guide barrel, the outside diameter and inside diameter of which intermediate segment essentially match the outside and inside diameters of the guide barrel, or clamping element, the end faces having a design complementary to the bordering end faces of the guide barrel, or clamping element. The bevels of the intermediate segment have an equidirectional orientation. With such an extractor it is possible to approximately triple the largest outside diameter in the area of the distal bevel of the guide barrel. The advantage of this is that a single extractor is suited for pulling electrodes with very different spiral diameters.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
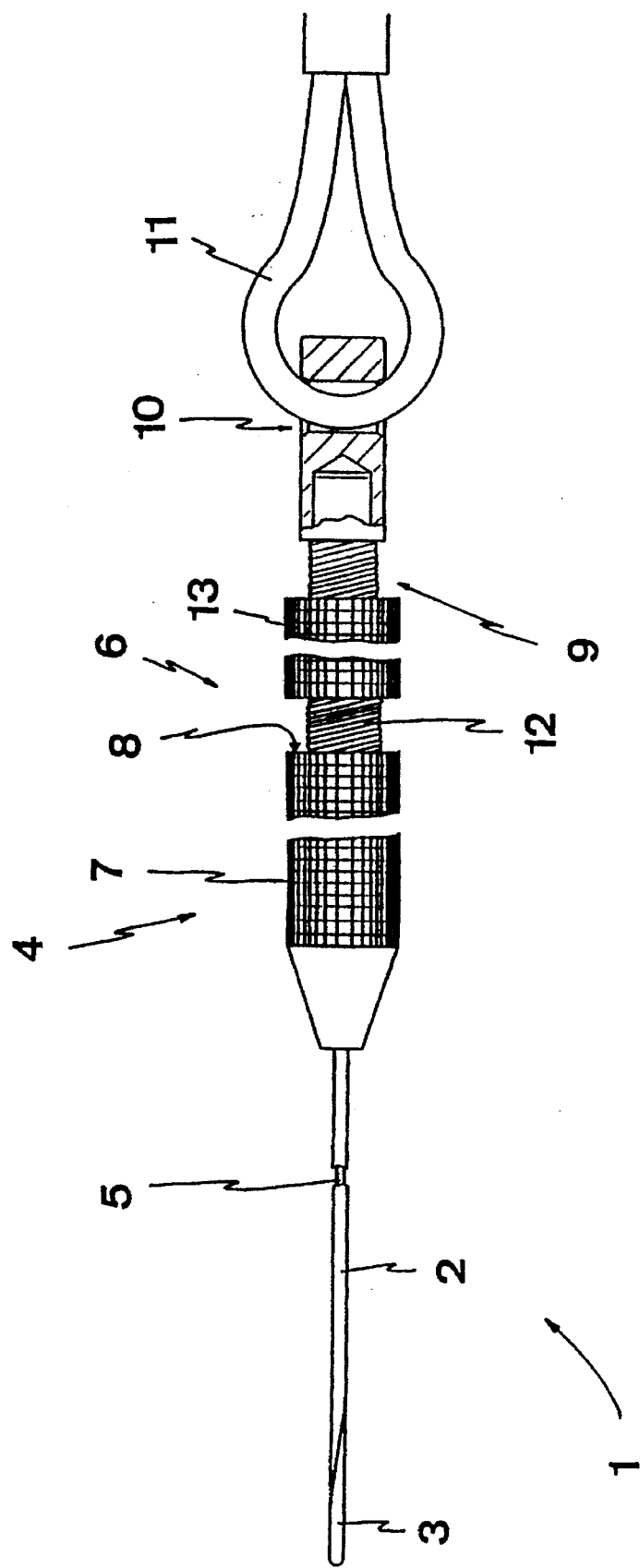
FIG. 1 represents, partly in section, a view of an extractor with a clamping element.

FIG. 1 shows the extractor 1 consisting essentially of a guide barrel 2 with a clamping element 3 arranged on its distal end and a handle element 4 on its proximal end. Inside the guide barrel 2 runs a pull wire 5 whose distal end is joined to the clamping element 3. On its proximal end, the pull wire 5 is retained by a chucking fixture 6.

The handle element 4 consists essentially of a cylindrical sleeve 7 whose outer surface is knurled to enhance the grip. Basing on the proximal end face 8 of the sleeve 7, a puller 9 can be screwed into the sleeve 7. On its end facing toward the guide barrel 2, the puller 9 engages the pull wire 5. Provided in the proximal area of the puller 9 is a bore 10 into which an eye 11 of a traction device can be inserted. A mounting nut 13 is arranged on the threaded section 12 of the puller 9 that protrudes out of the sleeve 7. The outer surface of the mounting nut 13 is knurled as well. Jammed onto the end face 8 of the sleeve 7, the nut 13 serves to secure the puller 9 in the sleeve 7.

Figure 2:
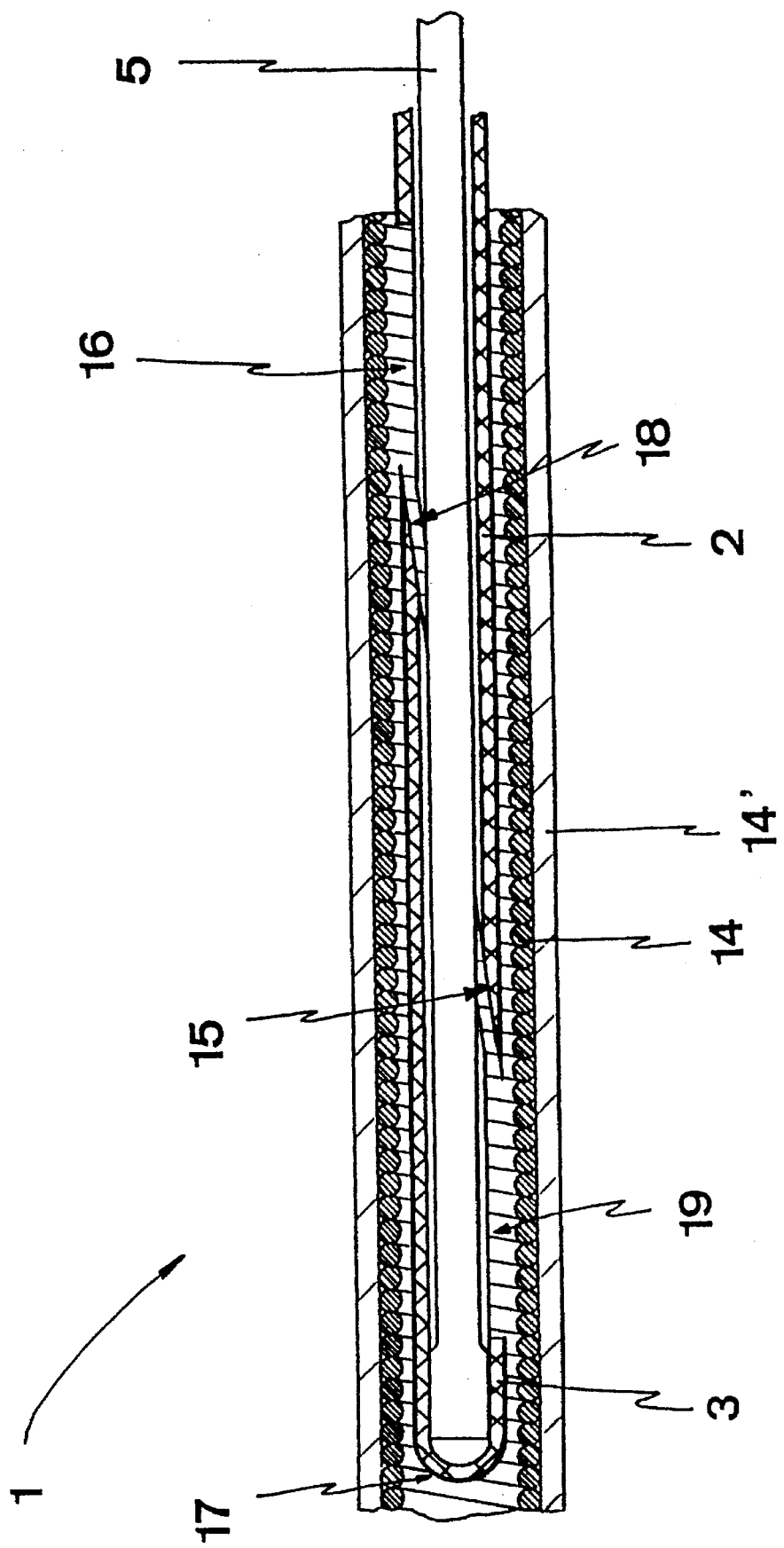
FIG. 2 represents the distal end of the extractor relative to FIG. 1 inserted in an electrode spiral, illustrated partly in longitudinal section.
Figure 3:
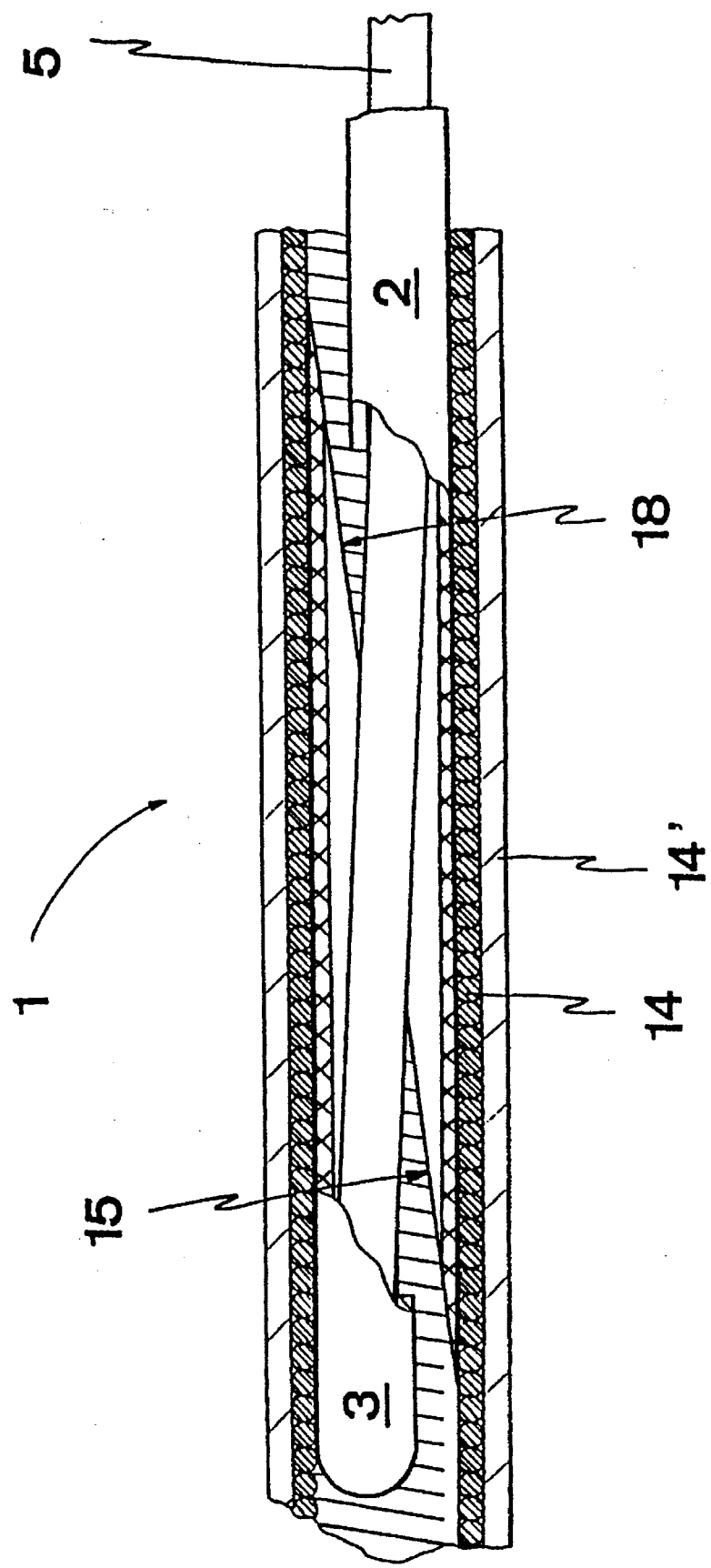
FIG. 3 represents the distal section of the extractor anchored in the electrode spiral relative to FIG. 2.

FIG. 2 shows the distal area of the extractor 1 inserted in an electrode spiral 14 of a cardiac pacemaker. The electrode spiral 14 is surrounded by an electrode insulation 14'. To illustrate the structure of the distal area of the guide barrel 2 and clamping element 3, these are slightly spaced in FIG. 2. During insertion into the electrode spiral 14, the clamping element 3 is arranged coaxially relative to the guide barrel 2.

The diameter of the pull wire 5 corresponds essentially to the inside diameter of the guide barrel 2, but leaves sufficient clearance to assure the movability of the pull wire also when the guide barrel 2 is bent sharply. Furthermore, the pull wire 5 possesses a sufficient flexural strength to allow insertion into electrode spirals 14 also with guide barrels 2 of greater length. The guide barrel 2 also has sufficiently flexural strength, so that it will not buckle in bellows fashion in the clamping procedure.

The guide barrel 2 features on its distal end a bevel 15 forming with the longitudinal axis of the guide barrel 2 an angle of about 7°. Basing on the area of the bevel 15 facing toward the handle element 4, a recess 16 is provided in the guide barrel 2. The width of the recess 16 matches essentially the diameter of the pull wire 5. The longitudinal extension of the recess 16 follows the longitudinal axis of the guide barrel 2.

The clamping element 3 is rounded on its distal end 17. On its proximal end, the clamping element 3 features a bevel 18, which in its design is complementary to the bevel 15 of the guide barrel 2, so that the bevels 15, 18 butt flush on each other. Basing on the area of the bevel 18 facing toward the distal end 17 of the clamping element 3, a recess 19 matching the recess 16 is provided in the clamping element 3.

The pull wire 5, guide barrel 2 and clamping element 3 are made of refined steel alloys. In the illustrated embodiment, the pull wire 5 is secured to the clamping element 3 by crimp joint. The pull wire 5 may also be joined to the clamping element 3 by laser welding.

In a further embodiment, the guide barrel 2 is made of a nitinol alloy, whereas the pull wire 5 and clamping element 3 are made of refined steel. The pull wire 5 is in this embodiment joined to the clamping element 3 by gluing.

In still another embodiment, both the guide barrel 2, clamping element 3 and pull wire 5 are made of a nitinol alloy.

When now exerting on the pull wire 5, and thus clamping element 3, a traction force by backing the puller 9 out of the sleeve 7 of the handle element 4, the clamping element 3 moves along the bevel 15 of the guide barrel 2 toward the handle element 4. The shallow angle inscribed by the bevels 15, 18 with the longitudinal axis of the guide barrel 2, or the longitudinal axis of the clamping element 3, assures that the clamping element 3 is being moved essentially parallel to its original coaxial arrangement with the guide barrel 2. Upon appropriate spreading of the clamping element 3 relative to the guide barrel 2, the areas of the guide barrel 2, or clamping element 3, which diametrically oppose the recess 16 and recess 19 bear on the inside of the electrode spiral 14. Backing the puller 9 farther out of the sleeve 7 now causes the clamping element 3 to be jammed on the guide barrel 2, inside the electrode spiral 14, so that the distal area of the extractor 1 is anchored in the electrode spiral 14 by frictional engagement.

To transmit a binding force sufficient to establish a frictional engagement between the clamping element 3 and guide barrel 2 with the electrode spiral 14, the shallow-angle arrangement of bevels 15, 18 has a favorable effect. Owing to the relatively long axial extension of bevels 15, 18, also the wall areas of the clamping element 3 and guide barrel 2 with which a frictional engagement of the electrode spiral 14 can be established are dimensioned appropriately large to provide already with relatively low pulling forces acting on the clamping element 3 an effective anchoring with the electrode spiral 14.

Upon application of a sufficient anchoring force, the mounting nut 13 is screwed onto the rear end face 8 of the sleeve 7 so as to secure the puller 9 in the sleeve 7. Using a pulling fixture whose eye 11 is fitted in the bore 10 of the puller 9, a traction force is then exerted on the entire extractor 1 in order to extract the electrode spiral 14 from the tissue surrounding the electrode spiral 14, or electrode insulation 14'.

Since the clamping element 3 and guide barrel 2 do not catch in the electrode spiral, the anchoring within electrode spiral 14 can be easily released again. Such anchoring release is necessary not only after successful extraction of the electrode spiral 14, but notably also in inserted state, if the electrode spiral 14, or electrode insulation 14', has already been overgrown by the tissue to a degree such that it can no longer be extracted readily and the surrounding tissue threatens to tear.

Figure 4:
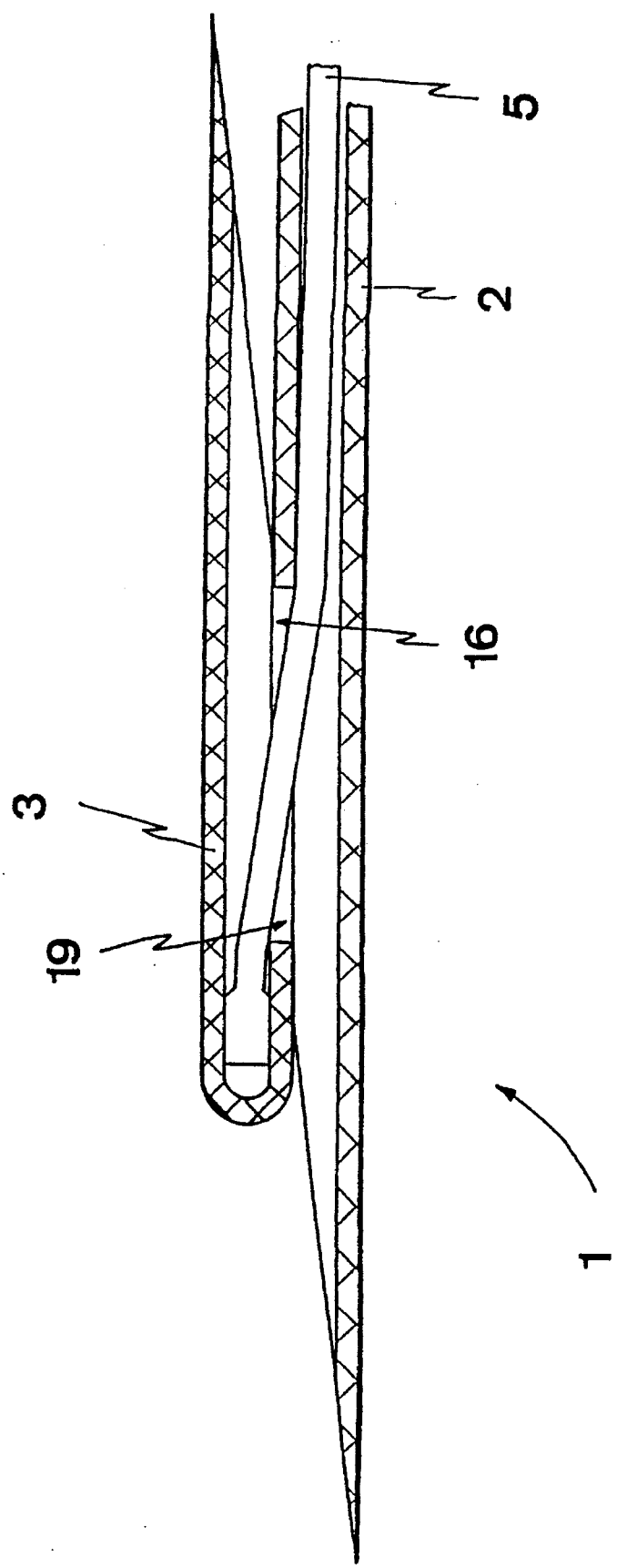
FIG. 4 represents the extractor relative to FIG. 1 in longitudinal section, with the clamping element offset by the maximum amount of offset.

FIG. 4 shows the distal area of the extractor 1 relative to FIG. 1 where the clamping element 3, by application of traction force on the pull wire 5, has been brought up into a position which maximally enlarges the greatest outside diameter of the guide barrel 2 in its distal area. From FIG. 4 it is evident that the pull wire 5 has in this position moved out both of recess 16 of the guide barrel 2 and of recess 19 of the clamping element 3. In this position, the outsides of guide barrel 2 and clamping element 3 border on each other.

Figure 5:
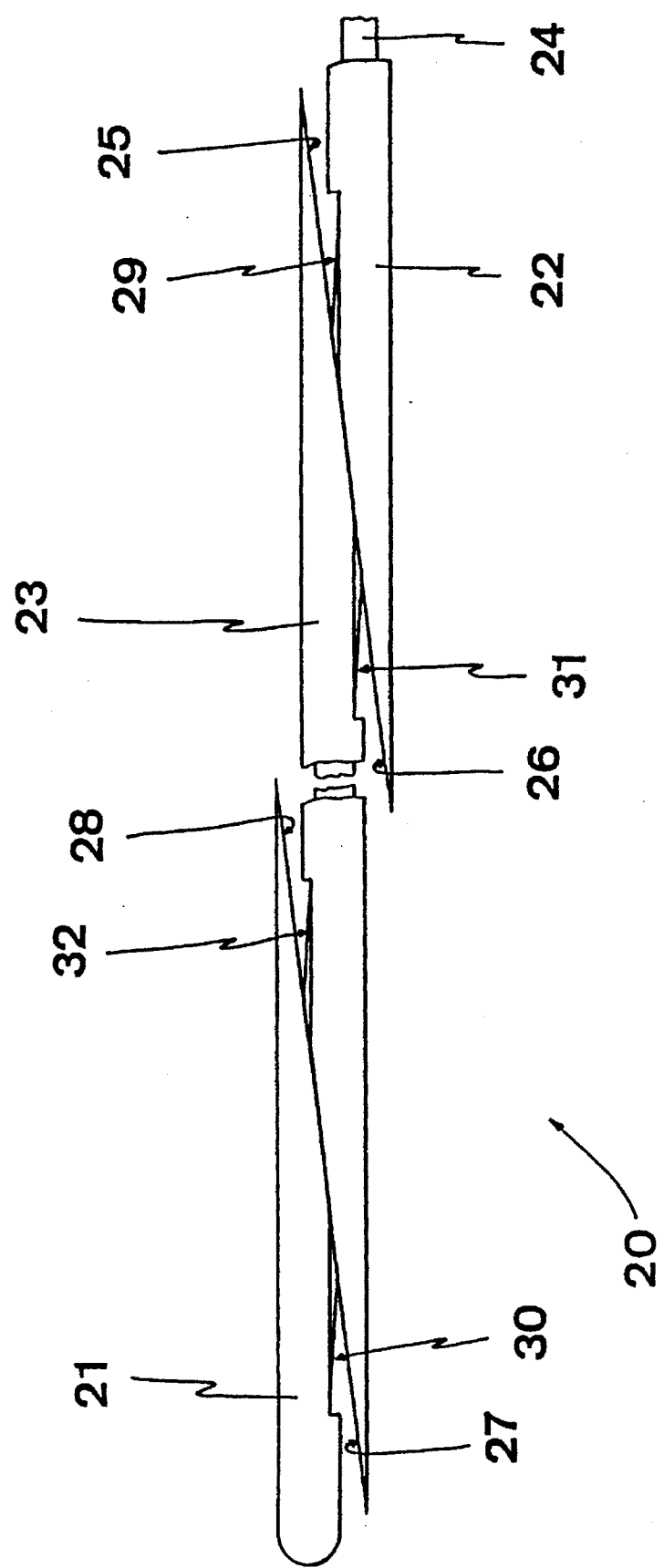
FIG. 5 represents an alternative embodiment with the extractor having an intermediate segment contained between the clamping element and the guide barrel.

The embodiment of FIG. 5 shows an extractor 20 with an intermediate segment 23 arranged between its clamping element 21 and guide barrel 22. Otherwise, the extractor 20 has the same features as extractor 1. The outside diameter and inside diameter of the intermediate segment 23 match those of the guide barrel 22. The pull wire 24 extends through the intermediate segment 23 and is secured to the clamping element 21.

The proximal end face 25 of the intermediate segment 23 is of a design complementary to the bevel 26 of guide barrel 22. The distal end face 27 of the intermediate segment 23 is in its design complementary to the bevel 28 of clamping element 21. Recesses 29, 30, 31, 32 corresponding to the recesses 16, 18 of the extractor are provided in the guide barrel 22, clamping element 21 as well as intermediate segment 23.

Depending on the length of the intermediate segment 23, different objectives can be achieved with the extractor 20. When the intermediate segment 23 is essentially twice as long as the clamping element 21, and thus of a relatively short design, the extractor 20 is suited notably for insertion in various electrode spirals differing in diameter. Possible tripling of the greatest outside diameter in the area of bevel 26 of the guide barrel 22 also allows insertion in relatively large electrode spirals.

With the intermediate segment 23 relatively long, two anchoring areas can be established within an electrode spiral 14 by exerting a traction force on the pull wire 24. Thereby, for instance with very soft electrode spirals, a frictional engagement can be established without unnecessarily widening the electrode spiral 14.

In another, not illustrated, embodiment a puller with an axial recess is provided, in lieu of the puller 9 in the handle element 4. This axial recess is engaged by a wedge which upon insertion allows moving the puller out of the handle element 4, so as to allow transmission of a traction force to the pull wire 5, 24.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An extractor, for extracting cardiac pacemaker electrodes implanted in tissue, said extractor comprising an elongated flexible guide barrel having a distal end and a proximal end, said proximal end joined to a handle element, said distal end having a beveled face which is angled relative to the longitudinal axis of the guide barrel, a pull wire disposed in the guide barrel and having a distal end, the distal end of the pull wire connected to a clamping element, said clamping element having a bevelled end face which is substantially complementary to and faces the bevelled distal end face of the guide barrel, a longitudinal recess in said guide barrel and oriented in the axial direction of the guide barrel, the length of the bevelled distal end face of the guide barrel in the axial direction of the guide barrel corresponding to a multiple of the outside diameter of the guide barrel.

2. The extractor according to claim 1, wherein the width of the recess is substantially equal to the diameter of the pull wire.

3. The extractor according to claim 1, wherein the bevelled distal end face of the guide barrel defines an angle of between 3° and 30° with the longitudinal axis of said guide barrel.

4. The extractor according to claim 3, wherein said angle is between 5° and 10°.

5. The extractor according to claim 1, wherein the diameter of the pull wire is substantially equal to the inside diameter of the guide barrel.

6. The extractor according to claim 1, wherein the clamping element comprises a section of the guide barrel.

7. The extractor according to claim 6, including a second longitudinal recess in the clamping element in the axial direction of the guide barrel, said second recess substantially corresponding to the recess in the guide barrel.

8. The extractor according to claim 1, including a tubular intermediate segment disposed between said clamping element and guide barrel, the outside and inside diameters of said segment respectively substantially equal to the outside and inside diameters of the guide barrel, said segment having bevelled end faces substantially complementary to the bevelled end faces of the guide barrel and clamping element.

9. The extractor according to claim 8, wherein the bevelled end faces of the segment have the same orientation relative to the longitudinal axis of the segment.

10. The extractor according to claim 1, wherein the guide barrel comprises a nitinol alloy and wherein the pull wire and clamping elements comprise refined steel.

* * * * *